United States Patent [19]

McNeil

[11] 4,354,932

[45] Oct. 19, 1982

[54] FLUID FLOW CONTROL DEVICE

[75] Inventor: Roderick J. McNeil, New Milford, Conn.

[73] Assignee: The Perkin-Elmer Corporation, Norwalk, Conn.

[21] Appl. No.: 197,302

[22] Filed: Oct. 15, 1980

[51] Int. Cl.³ .............................................. B01A 15/08
[52] U.S. Cl. ................................... 210/198.2; 55/386; 138/41; 210/291
[58] Field of Search .................. 138/40, 41; 210/198.2, 210/291; 55/386, 307, 308, 418, 419

[56] References Cited

U.S. PATENT DOCUMENTS

| | | | |
|---|---|---|---|
| 1,797,954 | 3/1931 | Greenwald | 138/40 X |
| 3,310,932 | 3/1967 | Melpolder | 55/386 |
| 3,398,512 | 8/1968 | Perkins, Jr. et al. | 55/386 |
| 3,453,811 | 7/1969 | Crowley | 55/386 |
| 4,025,432 | 5/1977 | Nolan et al. | 55/418 X |

OTHER PUBLICATIONS

Introduction to Modern Liquid Chromatography by Snyder and Kirkland, 2nd edition, John Wiley and Sons Inc., New York, pp. 228 and 229, 1979.

Primary Examiner—John Adee
Attorney, Agent, or Firm—S. A. Giarratana; F. L. Masselle; R. A. Hays

[57] ABSTRACT

A fluid flow control device useful for liquid chromatography includes a radial distribution plate having a patterned aperture therethrough which pattern is designed to ensure that every annulus of the distribution plate having a given area has the same uniform pressure when fluid flows therethrough. The radial distribution of a fluid throughout the aperture is created by a backpressure means adjacent the downstream surface of the radial distribution plate.

12 Claims, 2 Drawing Figures

FLUID FLOW CONTROL DEVICE

BACKGROUND OF THE INVENTION

The present invention generally relates to a fluid flow control device and, in particular, relates to such a device for producing a fluid flow having uniform pressure drop across the cross-section thereof.

The control of fluid flow, while of importance in many fields, is of primary importance in the field of liquid chromatography. In a liquid chromatography system a fluid, usually comprising a carrier fluid and a sample fluid, is injected into a separation column, such columns are generally known in the art. As well known, as the fluid passes through the column the constituents of the sample fluid travel therealong at different velocities due to their various rates of interaction with the packing material of the column. The intended result of this procedure is to provide an output flow of the various individual constituents one after the other. That is, the output of the column would initially contain only the least retained constituent and thereafter the next to the least retained constituent would flow out and etc. Ideally, there would be a sharp cut off at the interface between constituents. However, such is not always the case, for in conventional chromatography systems the transition from one constituent of the sample fluid to the next is often gradual and indistinct.

The transition problem between constituents can result from the fact that, in conventional columns, the fluid flow along the column is usually constrained to a core segment of the packing material. The effect of such a constraint is an inefficient separation of constituents. The inefficiency arises because the core segment quickly becomes saturated and constituents which should be slowed after traveling a certain length along the columns continue to flow since they cannot interact with the saturated packing material of the core segment. Thus the output of the constituents are, at the transitions therebetween, blended and indistinct. The capacity of the column for increased loads of the sample constituents is also impaired because only the core segment of the packing material is being utilized.

The constrained fluid flow through a liquid chromatography column also reduces the useful life of that column. The useful life of a given packing material is finite since, when a fluid is passed thereover, a small amount of the constituents of that fluid may be irreversibly retained. Thus the total amount of fluid passed over a portion of packing material throughout its useful life is also finite. Hence, it is easily understood that if, for a given cross-section of packing material, all the fluid passed thereacross is confined to a core segment thereof the useful life of that cross-section of material is less than if the same amount of fluid were distributed across the entire cross-section thereof.

SUMMARY OF THE INVENTION

In view of the foregoing discussion, it is one object of the present invention to provide fluid flow control device useful in conjunction with a liquid chromatography column to provide a fluid flow therein having a uniform pressure across the entire cross-section thereof. This object is accomplished by a fluid flow control device having a pressure distribution plate and a means for providing backpressure thereto.

It is another object of the present invention to provide a fluid flow control device adaptable for use with a liquid chromatography system to ensure that substantially all of the packing material in a given cross-section thereof is utilized.

These and other objects and advantages will become apparent from the following drawing and specification.

DETAILED DESCRIPTION OF THE INVENTION

Figure 1:
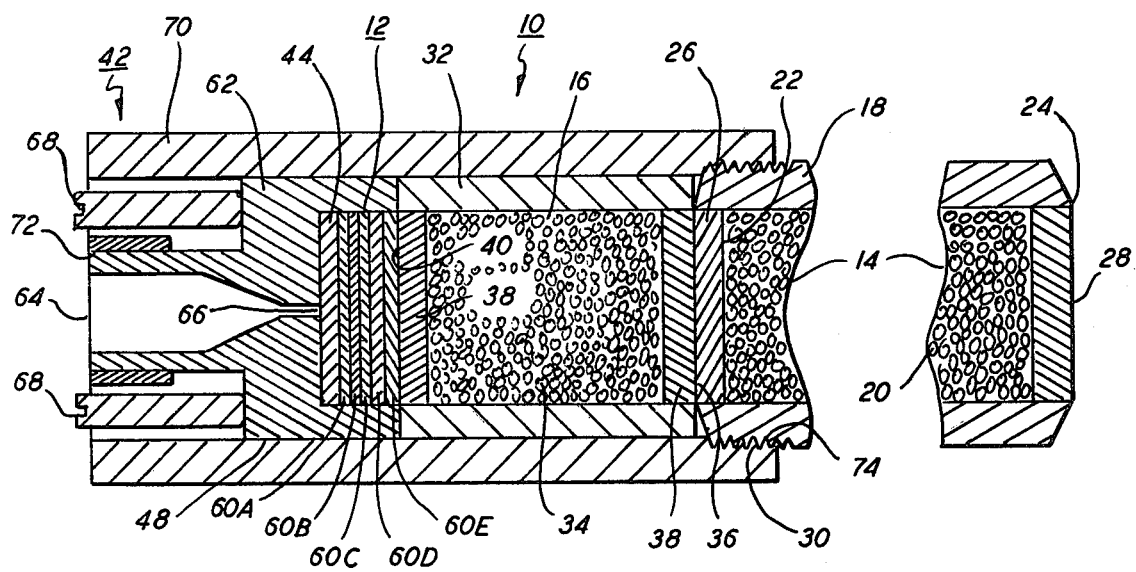
FIG. 1 is a cross-sectional view of a fluid flow control device, not drawn to scale, embodying the principles of the present invention.

An assembly, indicated generally at 10 in FIG. 1, of an exemplary system includes a fluid flow control device 12, incorporating the principles of the present invention, a liquid chromatography preparative column 14 and a chromatography guard column 16 between the device 12 and the preparative column 14. It should be apparent to those skilled in the art that the device 12 could be immediately adjacent the preparative column 14 is a guard column 16 is not used.

The liquid chromatography preparative column 14 includes a hollow body 18, usually cylindrical, packed with material 20 which controls the adsorption/partition of the various constituents of a sample and which can be silica or any other such material known in the art. At each end, 22 and 24 of the preparative column 14 there is a frit 26 and 28 respectively, which is used to retain the packing material 20 within the body 18. As more fully discussed below, the frit, 26 and 28, have a permeability which is substantially identical to that of the packed material 20. As used herein the term permeability refers to the capacity of a membrane, i.e. a frit, screen or bed of packing material, to allow the fluid of the chromatography system to penetrate or pass therethrough. Preferably, the porosity of the frits, 26 and 28, are dimensioned so as to retain the packing material 20. Further, as shown in FIG. 1, the preparative column 14 is provided with external threads 30 at one end 22 thereof.

The guard column 16 includes a hollow body 32, usually cylindrical, and is packed with material 34 having the same properties of the material 20 and which is usually identical to the material 20 of the column 14. At one end 36 of the body 32 the packing material 34 is retained by means of a frit 38 which has a permeability substantially identical to that of the packing material 34. The frit 38 is frictionally fitted to the one end 36 in a manner like that of frit 26 and 28 of the column 14. At the other end 40 of the guard column 16, i.e. the end distal from the preparative column 14, the packing material 34 is retained via a frit 38 as well as the device 12 which is secured in place by a cap assembly 42. As shown in FIG. 1, the cap assembly 42 also serves to hold the guard column 16 adjacent and aligned with the one end 22 of the preparative column 14. It has been found that a leakproof interface is formed with the end 22 of the column 14 if there is about a 3° bevel on the end 22.

The fluid flow control device 12 at the fluid entrance end 40 of the guard column 16 includes a radial distribution plate 44 having a patterned opening 46 therein. In addition, the device 12 includes a means 48 for creating a fluid backpressure at it's interface with the radial distribution plate 44. The means 48 is positioned downstream of the plate 44 and preferably abuts the downstream surface thereof.

Figure 2:
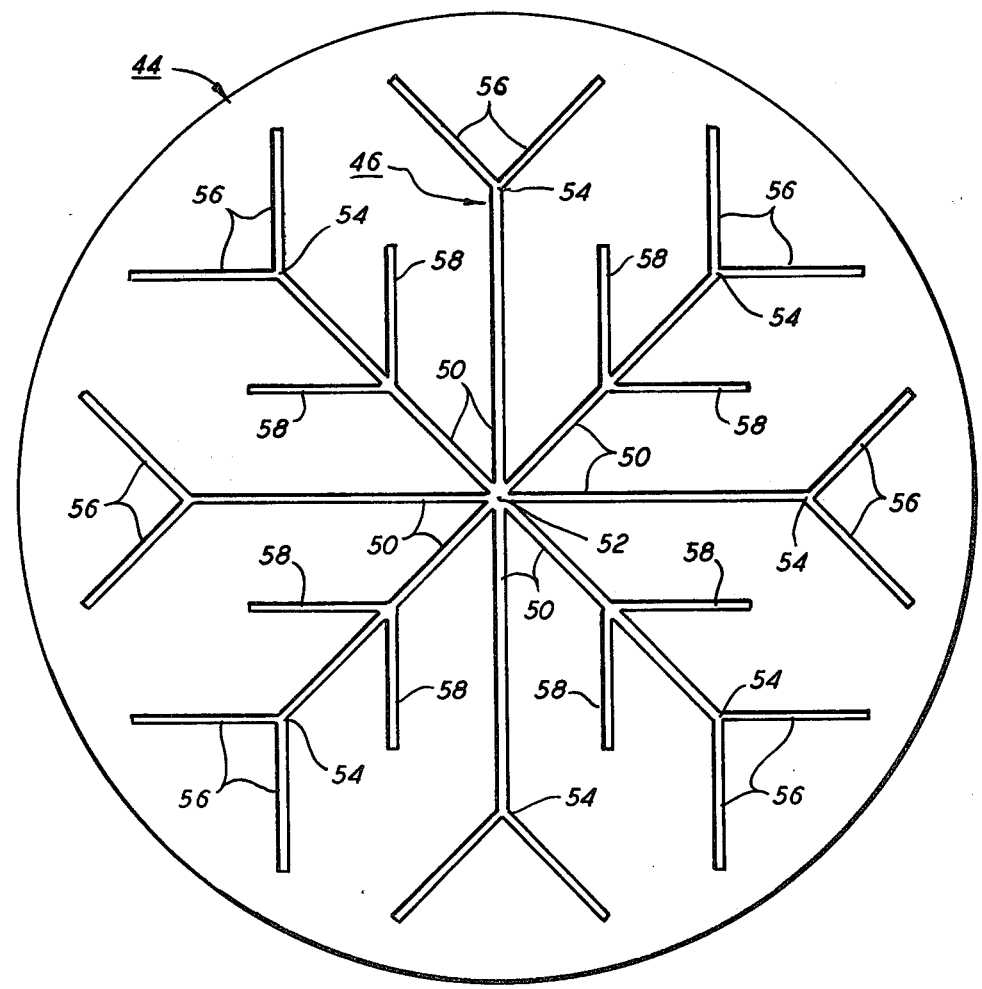
FIG. 2 is a plan view, also not drawn to scale, of one element of a fluid flow control device embodying the principles of the present invention.

The radial distribution plate 44 having the patterned opening 46 is characterized in that any annulus having the same area has the same porosity. As used herein the term permeability is used to indicate the proportion of the total area of the surface of the plate 44 occupied by the patterned opening. In operation, as more fully discussed below, any annulus selected has a uniform pressure drop therearound. In addition, every annulus containing a given area has the same uniform pressure drop therearound. One embodiment of a radial distribution plate 44 is shown in FIG. 2. As shown therein, the patterned opening 46 includes eight splines 50 radially extending from the center 52 of the plate 44. The splines are equally angularly spaced such that there is an angle of 45° between any two adjacent splines 50. The splines 50 extend a distance of 0.719 centimeters from the center 52. At the end 54 of each spline 50 distal from the center 52 there is a pair of first sub-splines 56 extending therefrom. Each pair of sub-splines 56 has an included angle of 90°. In addition, each pair of sub-splines 56 is symmetrically positioned with respect to the relevant spline 50. Further each sub-spline 56 is 0.373 centimeters long. In this embodiment the splines 50 and the sub-splines 56 are preferably 127 micrometers inches wide.

The distribution plate 44 also includes four pairs of second sub-splines 58. The four pairs extend from four of the splines 50 and are regularly distributed thereamong. That is, every other spline 50 has a pair of second sub-splines 58 extending therefrom at a point 0.358 centimeters from the center 52. As to the four relevant splines 50, the pairs of second sub-splines 58 extend symmetrically outward therefrom each at an angle of 45° to the relevant spline 50. Each second sub-spline 58 is 0.340 centimeters long and has a width which uniformly tapers from 165 micrometers at the spline to a width of 127 micrometers at the terminus thereof. In practice, the plate 44 is about 0.1 millimeter thick and is formed by known etching methods.

The means 48 for creating a fluid backpressure against the distribution plate 44 to force the radial distribution of the fluid is, in the embodiment, a series of four (4) screens 60. In order to ensure backpressure to force the radial flow of the injected fluid the means 48 is required to have a permeability which is less than the retention frit 38. Preferably, the screens 60A and 60B are 24×110 mesh, screen 60C has a 325×2300 mesh and screen 60D has a 60 mesh. Such a series of screens ensure that any fluid, having an entry pressure greater than about $22 \times 10^3$ N/m$^2$, is radially distributed through the opening 46 of the plate 44.

The cap assembly 42, as shown in FIG. 1, includes an injection plate 62 having a fluid entrance port 64 and a fluid exit port 66 which exit port 55 is immediately adjacent the center 52 of the distribution plate 44. The injection plate 62 is centrally secured via a plurality of holding screws 68 extending through a cover 70. The cover 70 has a central aperture 72 which provides access to the entrance port 64 of the injection plate 62. In this embodiment, the cover 70 is dimensioned so as to extend over the guard column 16 and threads onto the external threads 30 of the preparative column 14 via internal threads 74 provided in the cover 70. Of course, if the guard column 16 is not used the cover 70 would nevertheless be used to retain the device 12 in position adjacent the screen 26 at the one end 22 of preparative column 14.

In a specific operational example, the preparative column 14 is a 30.5 centimeter stainless steel cylinder having an inside diameter of 2.22 centimeters and an outside diameter of 3.49 centimeters. The guard column 16 is also a stainless steel cylinder having a 2.54 centimeter length, an inside diameter of 2.22 centimeters and an outside diameter of 2.86 centimeters. Both columns 14 and 16 are packed with silica particles having an average size of about 10 microns in a conventional manner and the retaining frits 26, 28 and 38 have about a 2 micron porosity. The frits 26, 28 and 38, as above-stated, have a permeability equivalent to the columns 14 and 16. Ordinarily this would not be possible since conventional columns, which do not utilize a fluid flow control device 12 embodying the principles of the present invention, require that the corresponding frits thereof provide some backpressure to assist radial distribution of the entering fluid. As stated above, this prior configuration is quite inefficient. Further, since the frits 26, 28 and 38 have the same permeability as the columns 14 and 16 the columns 14 and 16 can abut each other as there is no perturbations in the fluid flow across the frit interface.

In operation, the fluid is injected into the assembly 10, which can typically be a volume ranging from one ml to 100 ml, at a pressure ranging between about $27 \times 10^3$ N/m$^2$ to about $22 \times 10^4$ N/m$^2$. The backpressure means 48 described above, when the fluid impinges thereon, creates such a backpressure to the fluid that the fluid is forced radially outward across the distribution plate 44 which then supplies the fluid to the entire cross-section of the material 34 of the guard column 16. Because this is a closed system, once such a fluid distribution is created, that distribution extends for the entire length of the assembly 10. Thus, substantially all of the packing material 20 and 34 of both columns 14 and 16 is utilized to provide a highly efficient separation of constituents.

While the foregoing description is directed to a single embodiment other applications and modifications which do not deviate from the spirit and scope of the present invention will be recognized by those skilled in the art. Thus, the description provided above is exemplary only and the present invention is to be limited solely by the appended claims and the reasonable interpretation thereof.

What is claimed is:

1. A fluid flow control device comprising:
    a radial distribution plate having a patterned aperture therethrough, said aperture being characterized in that all annuluses thereof having the same area have the same permeability; and
    means, adjacent said plate, for creating a fluid backpressure thereagainst such that when fluid is introduced it is radially distributed across said plate.

2. A fluid flow control device as claimed in claim 1 wherein said means includes a plurality of screens.

3. A fluid flow control device as claimed in claim 2 wherein said plurality of screens is four.

4. A fluid flow control device as claimed in claim 3 wherein the screen adjacent said plate is 24×110 mesh and the remaining screens are, consecutively, 24×110 mesh, 325×2300 mesh and 60 mesh.

5. A fluid flow control device as claimed in claim 1 wherein said patterned aperture includes at least eight radial splines equally angularly spaced.

6. A fluid flow control device as claimed in claim 5 wherein each said spline has a pair of sub-splines extending symmetrically from the terminus thereof distal from the center of said plate.

7. A fluid flow control device as claimed in claim 6 wherein every other one of said splines has a pair of second sub-splines extending symmetrically therefrom at a point between said center of said plate and said terminus thereof.

8. An assembly comprising:
a liquid chromatography column, said column having packing material therein;
first means for retaining said packing material in said column, said first means having the same permeability as said packing material of said column; and
a fluid flow control device at one end of said column adjacent said retention means thereof, said device including a radial distribution plate having a patterned aperture therethrough which aperture being characterized in that all annuluses thereof having the same area have the same permeability and a means between said plate and said retention means for creating a fluid backpressure, said backpressure means having a comparatively lower permeability than said retention means.

9. An assembly as claimed in claim 8 further comprising:
a liquid chromatography guard column having packing material therein;
said guard column being positioned between said device and said liquid chromatography column; and
second means for retaining said packing material in said guard column, said second means having the same permeability as said packing material of said guard column.

10. An assembly as claimed in claim 9 wherein:
said packing material of said column and said packing material of said guard column have the same permeability.

11. An assembly as claimed in claims 8 or 9 wherein:
said retention means are frictionally fitted frits.

12. An assembly as claimed in claim 9 wherein:
said column and said guard column abut and thereby create an interface between one of said first retention means and one of said second retention means.

* * * * *

UNITED STATES PATENT AND TRADEMARK OFFICE
CERTIFICATE OF CORRECTION

PATENT NO. : 4,354,932
DATED : October 19, 1982
INVENTOR(S) : Roderick J. McNeil It is certified that error appears in the above-identified patent and that said Letters Patent is hereby corrected as shown below:

Column 2, line 25, "is", first occurrence, should read -- if --.

Column 3, line 7, "porosity" should read -- permeability --.

Signed and Sealed this

Thirty-first Day of January 1984

[SEAL]

Attest:

GERALD J. MOSSINGHOFF

Attesting Officer          Commissioner of Patents and Trademarks